United States Patent [19]

Finlay et al.

[11] 4,157,895
[45] Jun. 12, 1979

[54] RIA REAGENTS AND PROCESSES

[75] Inventors: Carole A. Finlay, Woburn; Marvin Mitchell, Watertown, both of Mass.

[73] Assignee: Nuclear International Corporation, Waltham, Mass.

[21] Appl. No.: 840,133

[22] Filed: Oct. 7, 1977

[51] Int. Cl.² .................. C09K 3/00; G01N 33/16
[52] U.S. Cl. ........................ 23/230 B; 252/408; 424/1; 422/56
[58] Field of Search ............ 23/230 B, 253 TP; 252/408; 424/1

[56] References Cited

U.S. PATENT DOCUMENTS

| | | | |
|---|---|---|---|
| 3,477,817 | 11/1969 | DeFalco | 23/230 B |
| 3,615,222 | 10/1971 | Mead | 23/230 B |
| 3,953,172 | 4/1976 | Shapiro et al. | 23/230 B |
| 3,964,865 | 6/1976 | Das | 23/230 B |
| 4,007,008 | 2/1977 | Becker et al. | 252/408 X |

Primary Examiner—Robert M. Reese
Attorney, Agent, or Firm—Cesari and McKenna

[57] ABSTRACT

This application relates to thyroxine ($T_4$) immunoassay procedures and, in particular, to the preparation of a novel filter-paper test substrate and a novel standard reagent used in preparation of the test substrate. The standard reagent used in preparation of the test substrate is prepared from commercially available materials and does not require the use of a human serum component.

9 Claims, 1 Drawing Figure

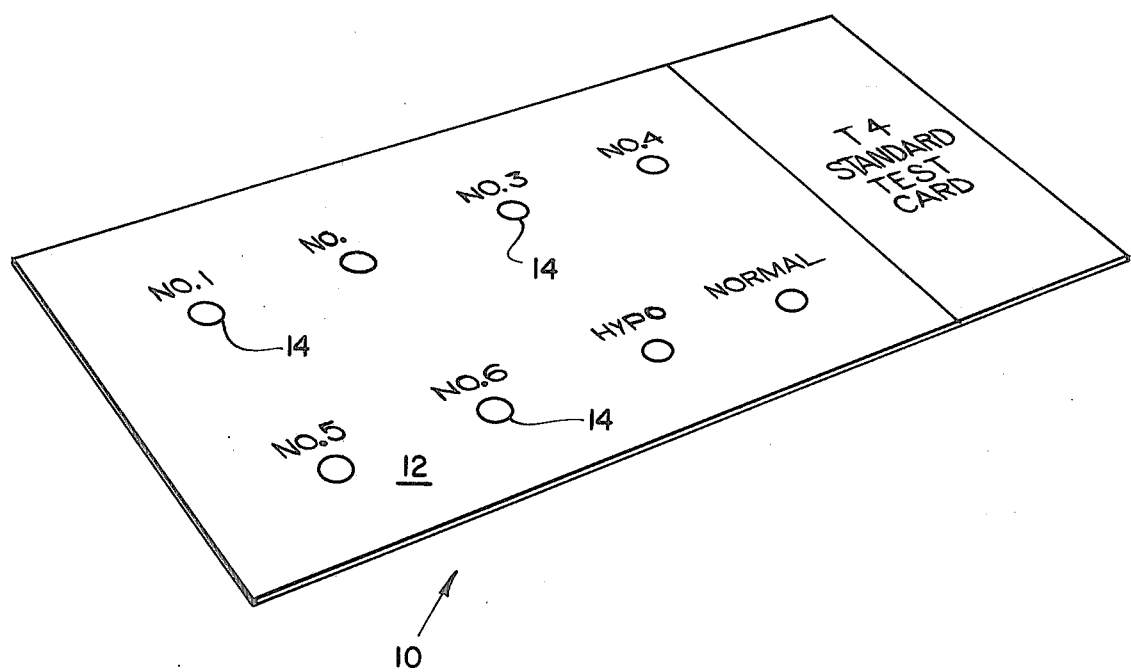

RIA REAGENTS AND PROCESSES

BACKGROUND OF THE INVENTION

This invention relates to novel materials and processes useful in immunoassay testing of thyroxine, henceforth usually referred to as $T_4$.

In recent years, it has been recognized that hypothyroidism in neonatal subjects is related to a relatively high incidence of mental retardation. For example, different studies have indicated that the incidence of such hypothyroidism is of the order of about 1 in each 5,000 to 10,000 births. However, early recognition of hypothyroidism and consequent treatment therefor can either prevent or ameliorate any mental retardation which might otherwise result. Consequently, large-scale screening of neonatal subjects is being carried out to determine the $T_4$ level of their blood. One general type of such a test is described by Larsen and Broskin in Pediatric Research, Volume 9, Pages 604-609 in an article entitled "Thyroxine $T_4$ Immunoassay Using Filter Paper Blood Sample for Screening of Neonates for Hypothyroidism." The test disclosed therein includes use of standard quantities of thyroxine distributed in small areas ("dots") of a filter paper.

These so-called "standard dots" are then used in assay procedures to determine the $T_4$ value of blood derived samples brought into contact therewith. This kind of test procedure is convenient to use for large-scale testing. Nevertheless, there have been substantial problems involved in obtaining inexpensive, dependable, easily absorbed, easily wetted, and easily processed standards.

The test employs the application of radioimmunoassay techniques to assess the concentration of neonatal thyroxine ($T_4$). The essential elements of this procedure are:

1. The development of an antibody, specific for $T_4$ and without significant cross reactivity with other substances.
2. Competition for a limited number of antibody binding sites between a radio-active isotope of $T_4$ and normal $T_4$.
3. Separation and determination of the two components once equilibrium has occurred.

In practice, known amounts of $T_4$ (standards) and unknown quantities of $T_4$ (samples), antiserum specific for $T_4$, and $^{125}I$-$T_4$ are incubated together. Once equilibrium is established the free hormone is separated from the hormone bound to the antiserum by the adsorption of the free to dextran-coated charcoal. The amount of bound $^{125}I$-$T_4$ present in the supernatant is determined with a gamma counter. Because stable $T_4$ is always present in greater concentration, the binding of $T_4$ $I^{125}$ to the antibody will be inhibited and the degree of inhibition will be proportional to the amount of stable $T_4$.

A standard curve can be established by measuring the fraction of antibody-bound $^{125}I$-$T_4$ after the addition of known concentrations of stable $T_4$.

The reaction can be represented by the equation:

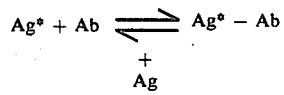

Where
- Ag* represents labeled antigen (hormone)
- Ag represents Unlabeled antigen (standard or unknown)
- Ab represents the specific antibody
- Ag-Ab represents unlabeled antibody-antigen complex
- Ag*-Ab represents labeled antibody-antigen complex.

In general, it is intended that the estimation of $T_4$ concentration be carried out in the capillary blood of neonatal subjects only. It is most advantageous as a preliminary diagnostic qualifying test. Results indicative of hypothyroidism should be combined with a TSH determination.

Although not directly relevant to the precise invention disclosed herein, a substantial amount of prior art relating to various immunoassay tests for $T_4$ is described in various U.S. patents classified in Class 424-1 of the U.S. Patent Office Manual of Classification.

SUMMARY OF THE INVENTION

It is principal object of the invention to provide a new and improved standard test substrate for use in immunoassay of $T_4$.

Another object of the invention is to provide a new standard impregnation composition for use in making said test substrate.

A further object of the invention is to provide an improved, inexpensive and easily wetted test standard.

Another object of the invention is to provide improved methods of making test standards for use in immunoassay procedure, particularly radio immunoassay (RIA) procedures.

Other objects of the invention will be obvious to those skilled in the art on their reading of this disclosure.

The above objects have been substantially achieved by using a synthetic hemoglobin solution which is free of a human serum component but contains the functional equivalent of such a serum so formulated that it will readily wet the test substrate card when it is applied thereto and also will be readily and completely wetted when subjected to the eventual assay procedure.

The above objects have been substantially achieved by utilizing, in the preparation of a standard test card, a series of standard $T_4$-bearing reagents comprising a known amount of $T_4$, hemoglobin, and bovine serum albumin as the principal physiologically-derived components thereof and, also, sufficient wetting agent, preferably a physiologically-derived wetting agent such as normal rabbit serum (NRS) to make the reagent one which readily wets the test substrate, particularly a cellulosic substrate, to which it is applied. Only a small amount of the NRS wetting agent is required, e.g. from about 1 to 3% by weight of the total albumin utilized.

ILLUSTRATIVE EMBODIMENT OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

IN THE DRAWING

FIG. 1 illustrates a test card, 10, prepared according to the invention. Card 10 comprises an absorbent cellulosic-paper substrate, 12, resembling ink-blotting paper and eight reagent-impregnated areas, 14, each of which contains a known quantity of $T_4$.

EXAMPLE

Standard compositions to be used in impregnating a test substrate are prepared from mixing a simulated human blood composition (Solution A) and a $T_4$ solution (Solution B).

Solution A is prepared as follows:

| Solution A | |
|---|---|
| hemoglobin: | 46.3 grams |
| bovine serum albumin: | 15.5 grams |
| normal rabbit serum: | 0.5 ml. |
| food coloring: | 10.2 ml. |
| aqueous solution of 0.9% NaCl stabilized with 0.01% sodium azide and adjusted to pH 10 with NaOH: | 426.0 ml. |
| aqueous solution of 10 N NaOH: | 74.0 ml. |

(The food coloring is cosmetic and preferably red food coloring such as that commonly available in food stores, e.g. that sold under the designation "Durkee's").

Solution A is formed by stirring the ingredients slowly at room temperature with a magnetic stirrer. Solution normally takes several hours and is stored at 4° C.

The hemoglobin and bovine serum materials are conveniently and preferably Fraction 5. As will be understood by those skilled in the art, the Solution A components should be substantially free of $T_4$.

SOLUTION B

Solution B is prepared from a number of stock solutions. The stock solutions are prepared as follows:

A $T_4$ methanol solution is prepared by dissolving one microgram of $T_4$ per 7.5 microliters of methanol. The methanol is added in a sealed serum vial with a small magnetic stirring bar. Stirring is carried out until the $T_4$ is completely dissolved. Thereupon the $T_4$ methanol solution is stored at −20° C.

A 0.9% NaCl; 0.01% $NaN_3$, 0.1% NRS stock solution is prepared by dissolving 9 grams of NaCl and 0.1 gram of $NaN_3$ in distilled water, bringing the total solution volume to 1 liter. The pH is adjusted to 10.0 with 1 N NaOH. Then 0.1 ml. normal rabbit serum (NRS) is added and well mixed into the solution.

Solution B is formed by placing the aforesaid NaCl/$NaN_3$/NRS stock solution in an ice bath for one hour and then adding 400 microliters of the $T_4$ methanol solution to 1572 microliters of the NaCl/$NaN_3$/NRS solution. The mixture, which has a $T_4$ concentration of 27 micrograms per milliliter, is sealed and put into an ice bath.

Solution A and Solution B are then utilized to form a number of so-called standard solutions. These standards, each containing a known amount of $T_4$ are those solutions which will be used to impregnate the test substrate "standard spots" as indicated in Table 1:

TABLE 1

| Standard Solution | Solution A ml. | Solution B ml. | Resultant Solutions $T_4$ Content | |
|---|---|---|---|---|
| No. 1 | 70 | 0 | 0 | |
| No. 2 | 120 | 60 | 13.5 | ng/ml |
| No. 3 | 69 | 70 | 27.4 | ng/ml |
| No. 4 | 63 | 140 | 60 | ng/ml |
| No. 5 | 120 | 400 | 90 | ng/ml |
| No. 6 | 63 | 350 | 150 | ng/ml |
| No. 7 | Hypothyroid | | 13.5 | ng/ml |
| No. 8 | Normal | | 90 | ng/ml |

PREPARATION OF TEST STANDARD CARD

Test substrates are support cards of the type commercially used in the analytical art for carrying test standards. For example, the cellulosic paper used in PKU testing procedures is entirely suitable. However, it should be realized that any inert, non-contaminating substrate capable of receiving the test standards and making them available in dried form for a subsequent test is suitable for use with the invention.

The support cards bear eight circular areas each identified with a reference number, as indicated in Table 1 and FIG. 1. The cards are arranged on racks so that these areas to be impregnated with standard solutions are not touching card other and are not in contact with the support surface; thus assuring that none of the solution will be allowed to seep by capillary action from the target areas.

About one to two hours before the application of the standard solutions to the cards, the solutions are mixed again on a magnetic stirring apparatus and then allowed to stand at room temperature, i.e. in a range of about from 15° C. to 25° C.

In practice, each standard solution will be applied to an area of the test card which is specifically identified for that particular solution. These areas will, typically, be a circle about 0.125 inch in diameter. About 4 to 5 ml. of the standard solution is first placed in a test tube. Then 50 microliters of each solution is placed carefully on its respective circle. The cards are allowed to dry under typical ambient conditions without exposure to heat and preferably without exposure to strong radiation such as direct sunlight.

Using the above procedures, excellent distribution of the standard solution is achieved within the circles. The standard solutions wet the circles and there are little or no non-wetted spots within the "stains" caused by the standard solution. The test cards prepared as described above are stored at 4° F. until they are required for shipment to the user.

The cards thus prepared are normally supplied as part of a kit to be used in otherwise well-established immunoassay tests. The most common test is a Radioimmunoasay (RIA) Test, but those skilled in the analytical arts will realize the principles of the invention can be applied also to preparation of test cards for use in fluorescent chemical-tagging test procedures of the type known in the art.

SAMPLE COLLECTION

A blood sample is collected from the neonatal subject. The blood sample is placed on a sample card, in an area of the card which is substantially larger than the target area on the test cards which have been treated with the standard solutions. The reason for this is that the sample card area will be used as the source of many cut-out samples, e.g. one for use with each standardized $T_4$-bearing target area of the test card.

THE ACTUAL TESTING

Eight test tubes are prepared, each for use with a standard dot prepared with a different $T_4$ level as described in Table 1. Each standard bearing area dot of the test card is punched into its respective tube.

One ml. of a salicylate-type body-tracer solution suitably buffered as with glycine acetate (all as well known in the art) is added to each test tube and mixed with the dot. During this time this procedure allows the displacement of thyroxine from thyroxine-binding globulin in the sample and allows it to interact with the body, i.e. a Rabbit anti-T antibody which is a component of he tracer as is known in the art. The resulting mixtures are stored for 18 to 24 hours at which time their ingredients are counted to determine the total count thereof, all as is presently well-known in the radio-immunoassay art.

Thereupon a milliliter of a cold dispersion of dextran-coated charcoal of the type known to the art is added to each tube. This procedure, also well known in the art, provides means for the non-bound antibody to be absorbed on the charcoal, leaving the bound antibody in the supernatant. The tubes with the various mixtures are shaken gently, placed in an ice-bath at 4° C. for 45 minutes, and then centrifuged at 2000 rpm for 15 minutes at 4° C. Identical volumes of supernatant liquids from each sample are counted for at least one minute in a gamma counter adjusted to $I^{125}$.

What we claim as new and desire to secure by Letters Patent of the United States is:

1. A human blood simulating reagent for use in impregnating a substrate with a known amount of $T_4$, said reagent comprising, in addition to a known amount of $T_4$, hemoglobin and bovine serum albumin as the principal physiologically-derived component thereof, said reagent additionally comprising sufficiently wetting agent to provide means effective to render a paper substrate impregnated with said reagents readily wettable of said reagent.

2. A reagent as defined in claim 1 wherein said wetting agent is a physiologically-derived blood serum fraction other than said bovine serum albumin.

3. A reagent as defined in claim 2 wherein said serum is normal rabbit serum and is less than about three percent by weight of said bovine serum albumin.

4. A test card of the type useful in detection of hypothyroidism bearing at least one area impregnated with a reagent comprising, in addition to a known amount of $T_4$, hemoglobin and bovine serum albumin as the principal physiologically-derived component thereof, said reagent additionally comprising sufficient wetting agent to provide means effective to render a paper substrate impregnated with said reagents readily wettable of said reagent.

5. A test card as defined in claim 4 wherein said wetting agent is a physiologically-derived blood serum fraction other than said bovine serum albumin.

6. A test card as defined in claim 4 wherein said wetting agent is a physiologically-derived blood serum fraction other than said bovine serum albumin.

7. An improved process for making a standard test card for use in $T_4$ assay procedures, said process comprising impregnation of said test card with a simulated blood mixture comprising a known amount of $T_4$, hemoglobin and bovine serum albumin as the major components thereof, and a quantity of wetting agent effective to make said substrate readily wettable by said simulated blood mixture.

8. A process as defined in claim 7 wherein said wetting agent is a physiologically-derived blood serum fraction other than said bovine serum albumin.

9. A process as defined in claim 8 wherein said serum is rabbit serum.

* * * * *